United States Patent
Danducci et al.

(10) Patent No.: US 11,244,280 B2
(45) Date of Patent: Feb. 8, 2022

(54) REDUCING FOOD WASTE BY USING A MACHINE LEARNING MODEL

(71) Applicant: INTERNATIONAL BUSINESS MACHINES CORPORATION, Armonk, NY (US)

(72) Inventors: Angelo Danducci, Austin, TX (US); Igor Ramos, Georgetown, TX (US); Denny Nguyen, Round Rock, TX (US)

(73) Assignee: International Business Machines Corporation, Armonk, NY (US)

( * ) Notice: Subject to any disclaimer, the term of this patent is extended or adjusted under 35 U.S.C. 154(b) by 353 days.

(21) Appl. No.: 16/356,056

(22) Filed: Mar. 18, 2019

(65) Prior Publication Data
US 2020/0302377 A1 Sep. 24, 2020

(51) Int. Cl.
G06Q 10/08 (2012.01)
G06Q 10/00 (2012.01)
G01N 33/02 (2006.01)
G06N 20/00 (2019.01)
G06Q 50/12 (2012.01)

(52) U.S. Cl.
CPC ........... *G06Q 10/087* (2013.01); *G01N 33/02* (2013.01); *G06N 20/00* (2019.01); *G06Q 10/30* (2013.01); *G06Q 50/12* (2013.01)

(58) Field of Classification Search
None
See application file for complete search history.

(56) References Cited

U.S. PATENT DOCUMENTS

| 7,849,902 | B2 | 12/2010 | Walker | |
|---|---|---|---|---|
| 2002/0161652 | A1 | 10/2002 | Paullin | |
| 2007/0221727 | A1 | 9/2007 | Reznik | |
| 2015/0051841 | A1* | 2/2015 | Minvielle | A23B 9/10 702/22 |
| 2016/0300285 | A1 | 10/2016 | Gandhi | |
| 2017/0076249 | A1* | 3/2017 | Byron | G06N 20/00 |
| 2018/0053140 | A1* | 2/2018 | Baca | G06Q 10/087 |
| 2018/0121961 | A1 | 5/2018 | Villanueva | |

FOREIGN PATENT DOCUMENTS

| CN | 101604470 B | 12/2009 |
|---|---|---|
| CN | 103995965 B | 8/2014 |

* cited by examiner

*Primary Examiner* — Paul Danneman
(74) *Attorney, Agent, or Firm* — Schmeiser, Olsen & Watts; Stephanie Carusillo

(57) ABSTRACT

An approach is provided for using a machine learning model to reduce food waste. Estimation models for food items are created by using a machine learning model. The estimation models have prediction functions specifying timelines during which the food items are not spoiled and are in a condition for consumption. Prediction function solutions are generated for a food item inventory to indicate menu items for respective time periods. Each menu item includes food item(s) which are in condition for consumption based on the estimation models. Menu recommendations corresponding to the time periods are generated. Each menu includes menu item(s) indicated by the prediction function solutions. The menu recommendations reduce a waste of the food items through spoilage by increasing a likelihood of consumption of the food items within the respective timelines.

17 Claims, 6 Drawing Sheets

REDUCING FOOD WASTE BY USING A MACHINE LEARNING MODEL

BACKGROUND

The present invention relates to reducing food waste, and more particularly to reducing food waste by using a machine learning model to make food utilization recommendations.

About one-third of the food produced in the world for human consumption every year is lost or wasted. In the United States, food waste is estimated at between 30-40 percent of the food supply. Food may be wasted due to improper storage conditions, remaining on the shelf at a retail grocer for too long, or being disposed of even though the food may still be appropriately used for alternative preparations.

Known food monitoring techniques calculate shelf life of food by monitoring conditions of the food. For example, a chill cabinet storing fruits and vegetables predicts a remaining shelf life of the fruits and vegetables, counts down the time until the end of the shelf life, and generates a locally-presented alarm in response to the remaining shelf life being less than 24 hours, thereby prompting a consumer to use the fruits and vegetables. As another example, a known shelf life warning system is based on modeling microorganism growth.

SUMMARY

In one embodiment, the present invention provides a method of using a machine learning model to reduce food waste. The method includes creating, by one or more processors, estimation models for respective food items by using a machine learning model that receives data from one or more sensors monitoring the food items. The estimation models have respective prediction functions. Each prediction function specifies one or more timelines during which a given food item is not spoiled and is in a condition for consumption using respective one or more methods of preparing the given food item. The method includes generating, by the one or more processors, solutions of the prediction functions for a specified inventory of the food items and specified periods of time. The solutions indicate menu items for respective periods of time. Each menu item includes one or more of the food items which are in the condition for consumption based on the timelines specified by the estimation models. The method further includes generating, by the one or more processors and based on the solutions of the prediction functions and the machine learning model, recommendations of menus corresponding to the specified periods of time. Each menu for a given period of time includes one or more of the menu items indicated by the solutions of the prediction functions. The recommendations of the menus reduce a waste of the food items through spoilage by increasing a likelihood of a consumption of the food items within the respective timelines.

In another embodiment, the present invention provides a computer program product for using a machine learning model to reduce food waste. The computer program product includes a computer readable storage medium having computer readable program code stored on the computer readable storage medium. The computer readable program code is executed by a central processing unit (CPU) of a computer system to cause the computer system to perform a method. The method includes the computer system creating estimation models for respective food items by using a machine learning model that receives data from one or more sensors monitoring the food items. The estimation models have respective prediction functions. Each prediction function specifies one or more timelines during which a given food item is not spoiled and is in a condition for consumption using respective one or more methods of preparing the given food item. The method further includes the computer system generating solutions of the prediction functions for a specified inventory of the food items and specified periods of time. The solutions indicate menu items for respective periods of time. Each menu item includes one or more of the food items which are in the condition for consumption based on the timelines specified by the estimation models. The method further includes based on the solutions of the prediction functions and the machine learning model, the computer system generating recommendations of menus corresponding to the specified periods of time. Each menu for a given period of time includes one or more of the menu items indicated by the solutions of the prediction functions. The recommendations of the menus reduce a waste of the food items through spoilage by increasing a likelihood of a consumption of the food items within the respective timelines.

In another embodiment, the present invention provides a computer system including a central processing unit (CPU); a memory coupled to the CPU; and a computer readable storage device coupled to the CPU. The storage device includes instructions that are executed by the CPU via the memory to implement a method of using a machine learning model to reduce food waste. The method includes the computer system creating estimation models for respective food items by using a machine learning model that receives data from one or more sensors monitoring the food items. The estimation models have respective prediction functions. Each prediction function specifies one or more timelines during which a given food item is not spoiled and is in a condition for consumption using respective one or more methods of preparing the given food item. The method further includes the computer system generating solutions of the prediction functions for a specified inventory of the food items and specified periods of time. The solutions indicate menu items for respective periods of time. Each menu item includes one or more of the food items which are in the condition for consumption based on the timelines specified by the estimation models. The method further includes based on the solutions of the prediction functions and the machine learning model, the computer system generating recommendations of menus corresponding to the specified periods of time. Each menu for a given period of time includes one or more of the menu items indicated by the solutions of the prediction functions. The recommendations of the menus reduce a waste of the food items through spoilage by increasing a likelihood of a consumption of the food items within the respective timelines.

DETAILED DESCRIPTION

Overview

Known food management techniques result in a significant amount of food wasted due to improper storage conditions, remaining on the shelf for sale for too long, or being discarded even though the food may still be usable in an alternative method of preparation. Existing food management solutions focus on a limited number of sensors for determining shelf life of food. The existing solutions rely on locally presented alerts, such as an alarm on a device or an attached screen which is in close proximity to the monitored food. Furthermore, known food management solutions recommend consuming a food item in isolation (i.e., without regard to the food item being used together with other food items in meal preparation). The unique challenges of the known solutions that are described above are addressed by embodiments of the present invention.

Embodiments of the present invention use a machine learning model that implements visual recognition and a classification algorithm to classify states of food items and uses the food item classifications to estimate remaining shelf life of the food items and generate utilization recommendations for the food items. In one embodiment, a deep learning neural network that includes supervised learning receives input data from sensors that monitor the environmental conditions and attributes of food items and applies predictive models to recommend actions that a user can take in the future relative to the food items, so that consumption of the food items is increased, and spoilage of the food items is decreased.

In one embodiment, a utilization recommendation for a given food item includes a recommendation for a restaurant's menu items or for a recipe for preparing a meal that includes using the given food item and is based on an entire inventory consisting of a variety of food items. Based on a given inventory of food items in a restaurant and menu items typically offered by the restaurant, embodiments of the present invention create estimation models that estimate the remaining shelf life of the food items. Using output of the estimation models, embodiments of the present invention generate recommendations of specific menus for specific time periods that increase a likelihood that the food items in the given inventory are consumed by customers of the restaurant, thereby decreasing food waste due to spoilage of some or all of the food items.

In one embodiment, a notification of an impending end of a shelf life of a food item is stored in a cloud server and is accessed via a web browser. Alternatively, the aforementioned notification is sent to a user's application on a mobile device via a short message service (SMS) or a Push notification.

System for Reducing Food Waste Using a Machine Learning Model

Figure 1:
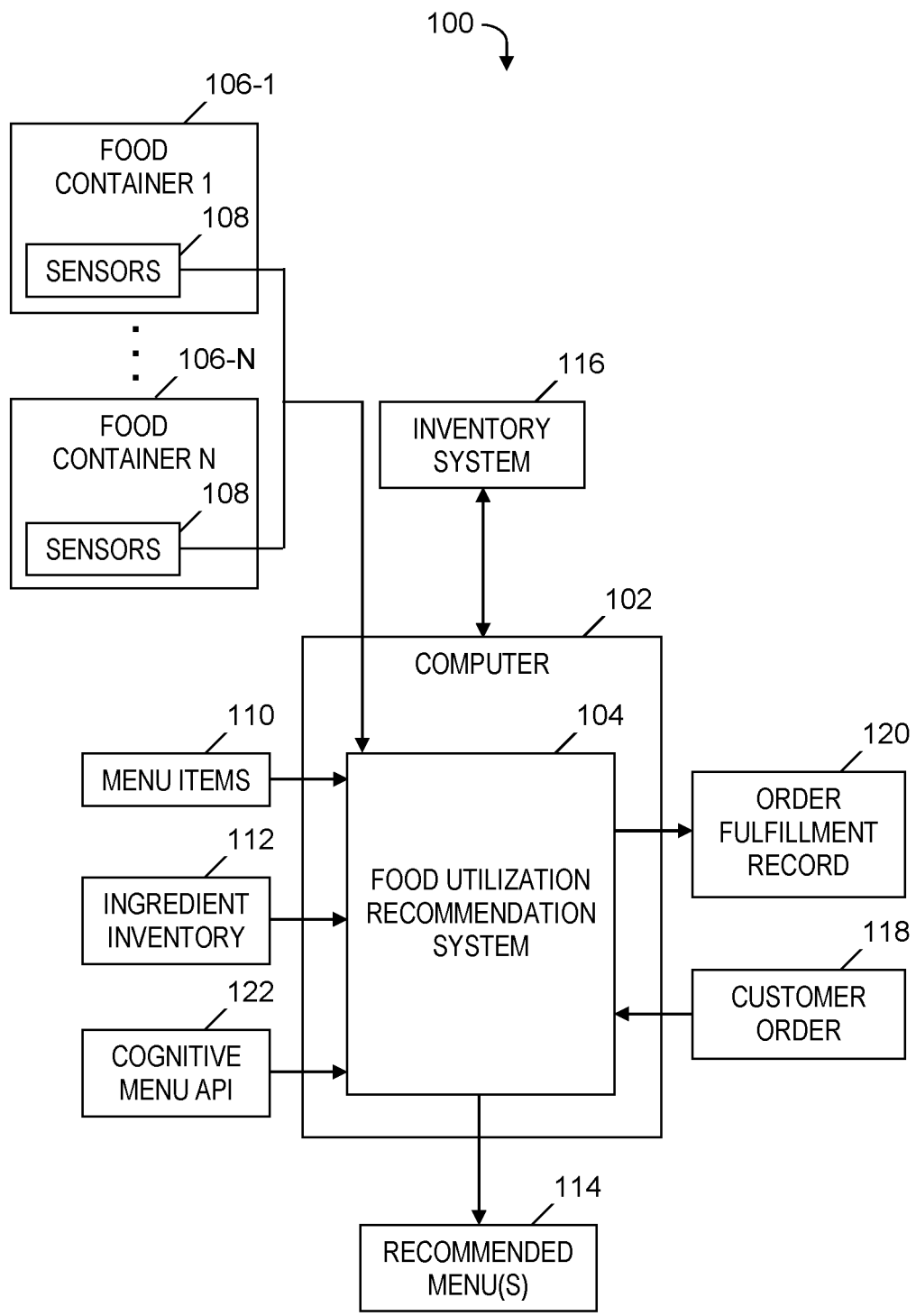
FIG. 1 is a block diagram of a system for reducing food waste using a machine learning model, in accordance with embodiments of the present invention.

FIG. 1 is a block diagram of a system 100 for reducing food waste using a machine learning model, in accordance with embodiments of the present invention. System 100 includes a computer 102, which executes a software-based food utilization recommendation system 104, which creates estimation models for food items (not shown) stored in food container 106-1, . . . , food container 106-N (or another set of food container(s) that are not shown), where N is an integer greater than or equal to one. Each food container includes or is operatively coupled to sensors 108. Although sensors 108 are included in each of the food containers, other embodiments include the same or different sets of sensors in each of the food containers.

In an alternate embodiment, any or all of the food containers in system 100 may be replaced with devices (not shown) that are embedded in the food items, where the devices include sensors 108.

Sensors 108 detect and measure conditions of an environment of a food item (also known as "environmental conditions" of the food item) and/or attributes of the food item included in a given food container. In one embodiment, sensors 108 in a given food container (e.g., food container 106-1) detect and measure a combination of (1) attributes of a food item: a color of the food item stored in the given food container, a pattern on the surface of the food item, a firmness of the food item, an identification of and an amount of an emission of one or more gases from the food item, a percentage of light reflected from the food item and (2) environmental conditions of the food item: the air temperature inside the given food container, the humidity inside the given food container, and an amount of light to which the given food container or the food item is exposed.

In one embodiment, sensors 108 transmit the measurements of the environmental conditions and attributes of the food items to a local computer gateway (not shown), which re-transmits the measurements to a cloud server that includes computer 102 and food utilization recommendation system 104. Computer 102 stores the measurements from sensors 108 in a data repository (not shown) and food utilization recommendation system 104 generates estimation models (i.e., predication models) (not shown) based on the measurements and uses the estimation models to estimate remaining shelf life for each of the food items. For a given type of food item stored in one or more of food containers 106-1, . . . , 106-N, the given type of food item is associated with a particular estimation model. For a given food container included in food containers 106-1, . . . , 106-N, the given food container is associated with a corresponding instance of a particular estimation model that is associated with the type of food item that is stored in the food container.

In one embodiment, food utilization recommendation system 104 generates an estimation model that uses a machine learning tool that employs visual recognition in a training phase to obtain images (i.e., training images) of a food item at different times and classify consumption states of the food item at the different times based on the appearance of the food item in the images, where each of the consumption states of the food item indicates whether the food item is suitable or unsuitable for consumption. In one embodiment, food utilization recommendation system 104 employs supervised learning to classify the consumption states by receiving input from human(s) who determine whether the food item is suitable or unsuitable for consumption by visual inspection of the food item, tasting the food item, or by any other means including using additional sensor(s) that are not included in or coupled to the food container.

During the training phase, food utilization recommendation system 104 also obtains the measurements of the environmental conditions and attributes of the food item from sensors 108. The estimation model generated by food utilization recommendation system 104 uses the classification of the consumption states and the measurements obtained during the training phase as input. After the training phase, for a given food item, the estimation model outputs a current consumption state of the given food item and a remaining amount of time before the food item is unsuitable for consumption (i.e., the remaining shelf life of the food item) based on matching an image of the given food item to one of the training images. For a food item that can be used in more than one food preparation method, the output of the estimation model is in an array that lists the consumption state and remaining shelf life for each of the possible food preparation methods.

After completion of the training phase, food utilization recommendation system 104 integrates multiple estimations of remaining shelf life for multiple food items into recommendations for menu items on menus to be offered to customers, so that food waste through spoilage is decreased by increasing a likelihood that the food items are consumed by the customers during the remaining shelf lives of the food items. For food items stored in food containers 106-1, ..., 106-N, food utilization recommendation system 104 receives measurements of the environmental conditions and attributes of the food items from sensors 108. Each of the food containers 106-1, ..., 106-N is instrumented with a particular set of sensors 108 to monitor the environmental conditions and attributes of a specific type of food item. For example, food container A is instrumented for bananas and food container B is instrumented for apples. Food containers 106-1, ..., 106-N may include multiple food containers of a single type. For example, food container A1 and food container A2 are both instrumented for bananas.

Each food container outputs a set of measurements that is received as input into an estimation model designed for a specific type of food item. For example, Model A receives input from the food container(s) that are instrumented for bananas. A particular instance of an estimation model receives measurements from a particular food container, thereby providing an instance of the estimation model with historical data (i.e., a memory) about the previous states of the food item, which provides a better prediction of remaining shelf life versus a stateless model. For example, Model instance A1 receives measurements from food container A1 and Model instance A2 receives measurements from food container A2, where food containers A1 and A2 are instrumented for bananas.

To generate a menu item-level recommendation, food utilization recommendation system 104 receives a list of known menu items 110. For example, menu items 110 may be a list of menu items that were used on menus previously offered by a restaurant that is using food utilization recommendation system 104. Food utilization recommendation system 104 also receives an ingredient inventory 112, which includes the names of food items that the restaurant has in its food inventory, the quantities of the food items in the food inventory, and prediction functions solved for different times of interest to the restaurant. The prediction functions are included in the estimation models generated by the food utilization recommendation system 104. A prediction function for a food item specifies timeline(s) during which the food item is suitable for consumption by respective food preparation method(s).

Food utilization recommendation system 104 matches the food items in ingredient inventory 112 to menu items included in menu items 110, where the matching menu items use the food items in ingredient inventory 112. Based on the matched menu items and the solutions of the prediction functions, food utilization recommendation system 104 generates recommended menu(s) 114 for the different times of interest to the restaurant which increases a likelihood that the food items in the menu items on the recommended menu(s) are consumed during the timelines specified by the prediction functions. Food utilization recommendation system 104 also generates a menu inventory associated with the recommended menu(s) 114, where the menu inventory specifies how many of each menu item on the recommended menu(s) 114 is available for sale at the restaurant at the times of interest.

In one embodiment, the generation of recommended menu(s) 114 by food utilization recommendation system 104 is also based on a prediction of consumption of particular menu items received by computer 102 from an inventory system 116, which generates the prediction based on a taste profile of customers of the restaurant. In one embodiment, inventory system 116 is included in an enterprise resource planning system.

In response to a customer of the restaurant placing an order for menu item(s) on one of the recommended menu(s) 114, food utilization recommendation system 104 receives a customer order 118 specifying the order for the menu item(s). In response to the customer's order being fulfilled, food utilization recommendation system 104 generates an order fulfillment record 120. Based on customer orders and order fulfillments, food utilization recommendation system 104 updates the ingredient inventory currently available to the restaurant and generates a recommendation for reordering ingredients that are below respective threshold amounts. Food utilization recommendation system 104 sends the recommendation for reordering ingredients to inventory system 116.

In one embodiment, in addition to fulfilling the recommended menu, food utilization recommendation system 104 uses the remaining inventory (i.e., the inventory of food items after the menu inventory is subtracted from the initial ingredient inventory) to create special menu item(s) (e.g., a house special) that had not been included in menu items 110. Cognitive menu application programming interface (API) 122 takes the remaining inventory as input and matches the remaining inventory to one or more recipes in a corpus of known recipes to determine a use of the remaining inventory as special menu item(s) which minimizes a waste of the remaining inventory through spoilage by increasing a likelihood that the remaining inventory is consumed by customers who order and consume the special menu item(s) during the shelf lives of the food items in the remaining inventory. Cognitive menu API 122 is a system that can generate a recipe given a list of ingredients.

In one embodiment, food utilization recommendation system 104 is part of a food management system which would generate recommended food preparation methods for available food items for times in the future, taking into account the times when ingredients that are ordered are expected to arrive according to inventory system 116. In one embodiment, food utilization recommendation system 104 calculates ingredients that are currently missing but are needed for recommended menu(s) for times in the future and generates a recommendation to reorder those currently missing ingredients. Food utilization recommendation system 104 bases the recommendation to reorder in part on the predicted restaurant consumption profile provided by inventory system 116 and how much of a given dish is expected to sell on a given day.

In one embodiment, food containers 106-1, ..., 106-N are used by a single restaurant. In another embodiment, mutually exclusive sets of food containers included in food containers 106-1, ..., 106-N are used by respective restaurants.

The functionality of the components shown in FIG. 1 is described in more detail in the discussion of FIG. 2, FIG. 3, FIG. 4, FIG. 5, and FIG. 6 presented below.

Process for Reducing Food Waste Using a Machine Learning Model

Figure 2:
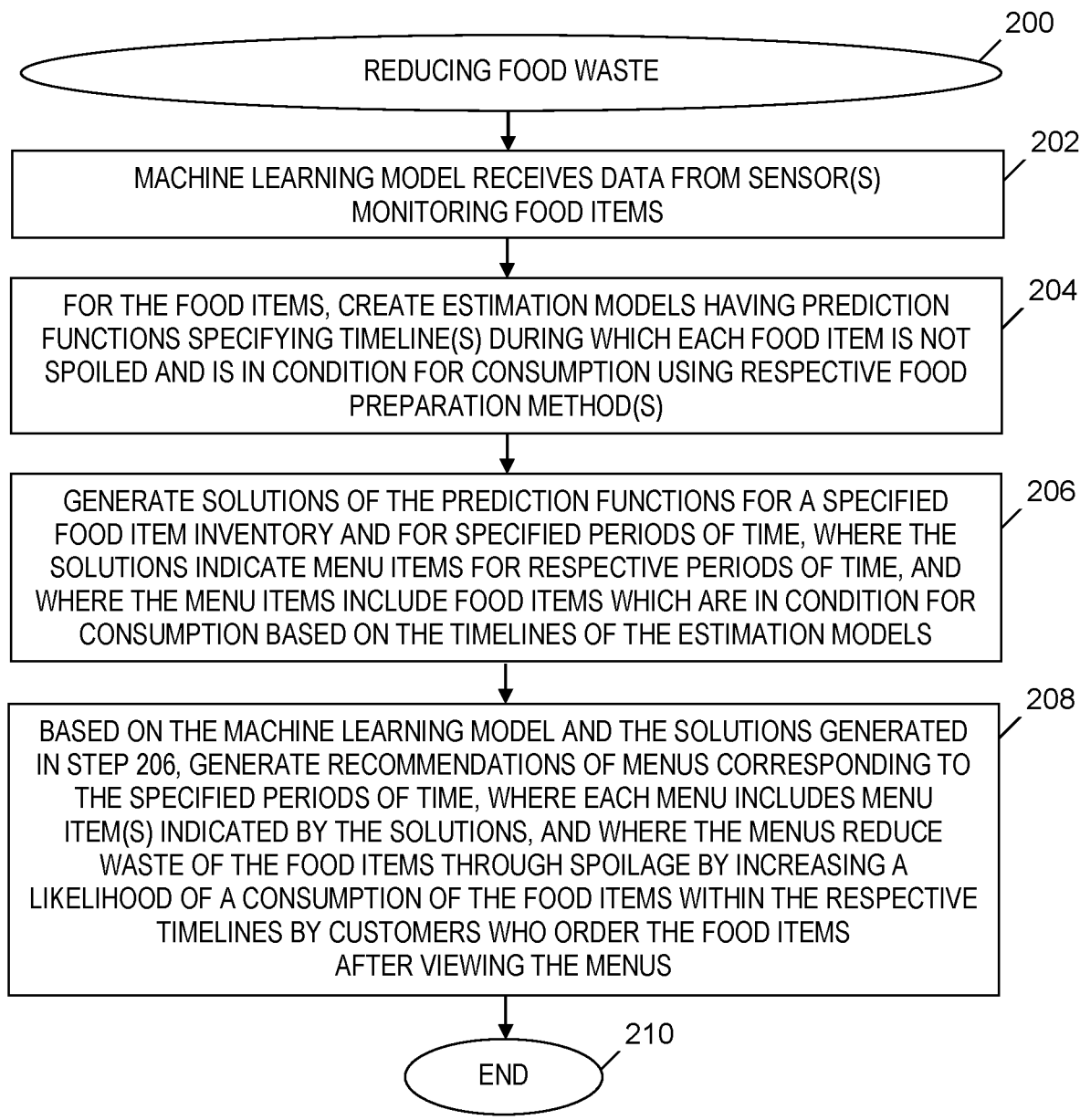
FIG. 2 is a flowchart of a process of reducing food waste using a machine learning model, where the process is implemented in the system of FIG. 1, in accordance with embodiments of the present invention.

FIG. 2 is a flowchart of a process of recommending food utilization to reduce food waste, where the process is implemented in the system of FIG. 1, in accordance with embodiments of the present invention. The process of FIG. 2 starts at step 200. In step 202, a machine learning model included in food utilization recommendation system 104 (see FIG. 1) receives data from sensors 108 (see FIG. 1) monitoring food items. The data from the sensors 108 (see FIG. 1) includes measurements of environmental conditions of the food items (e.g., temperature and humidity of the air in a food container that stores a food item and an amount of light to which the food item is exposed) and/or measurements attributes of the food items (e.g., a color of the food item, a pattern on the food item, an amount of firmness of the food item, an amount and an identification of gas(es) emitted from the food item).

In step 204, food utilization recommendation system 104 (see FIG. 1) creates estimation models for the food items, each food item corresponding to an instance of an estimation model, and each estimation model corresponding to a type of food item. An estimation model includes a prediction function that specifies timeline(s) during which a given food item is not spoiled and is in condition for consumption.

In cases in which a given food item can be used in more than one food preparation method, then the estimation model specifies multiple timelines for the given food item. The timelines specify the times during which the given food item, when prepared using respective food preparation methods, is suitable for consumption and is not spoiled.

In one embodiment, steps 202 and 204 collectively include the process of FIG. 3, which is discussed below.

In step 206, food utilization recommendation system 104 (see FIG. 1) generates solutions of the prediction functions included in the estimation models associated with the food items. food utilization recommendation system 104 (see FIG. 1) generates the solutions of the prediction functions for a specified inventory of food items included in ingredient inventory 112 (see FIG. 1) and for specified periods of time. In one embodiment, the specified periods of time are specified as being periods of time during which different menus of a restaurant will be available to customers of the restaurant, where the food utilization recommendation system 104 (see FIG. 1) selects the different menus of the restaurant from recommended menu(s) 114 (see FIG. 1).

The solutions of the predication functions indicate menu items for the respective periods of time, where the menu items include the food items, which are suitable for consumption based on the timelines of the estimation models, where the timelines include the specified periods of time.

In step 208, based on the machine learning model and the solutions generated in step 206, food utilization recommendation system 104 (see FIG. 1) generates recommended menu(s) 114 (see FIG. 1) corresponding to the specified periods of time. Each of the recommended menu(s) 114 (see FIG. 1) includes menu item(s) indicated by the solutions generated in step 206. The recommended menu(s) 114 (see FIG. 1) reduce a waste of the food items through spoilage by increasing a likelihood of a consumption of the food items within the respective timelines by customers of the restaurant who order the food items after viewing the recommended menu(s) 114 (see FIG. 1).

The process of FIG. 2 ends at step 210.

In one embodiment, food utilization recommendation system 104 (see FIG. 1) determines an adjustment has been made to an environment of a food item being stored in food container 106-1 (see FIG. 1). The adjustment is a change in one or more of the following environmental conditions: the air temperature within the food container 106-1 (see FIG. 1), the humidity within the food container 106-1 (see FIG. 1), and an amount of light to which the food item is exposed. Using a classification algorithm, food utilization recommendation system 104 (see FIG. 1) determines that the adjustment to the environment of the food item extends the shelf life of the food item and prevents the spoilage of the food item beyond a time at which spoilage of the food item was previously predicted in step 206, which is determined by a prediction function in an estimation model without taking into account the adjustment to the environment. The food utilization recommendation system 104 (see FIG. 1) generates updated recommended menu(s) based on the extended shelf life of the food item, which is based on the adjustment to the environment of the food item.

In one embodiment, food utilization recommendation system 104 (see FIG. 1) determines that one or more food items stored in one or more food containers included in food containers 106-1, ..., 106-N (see FIG. 1) have a measurement of an attribute that is within a threshold amount of a level of freshness, a level of staleness, a predicted shelf life, and a predicted time of spoilage. The food utilization recommendation system 104 (see FIG. 1) determines one or more recipes that use the one or more food items having the measurement of an attribute that is within the threshold amount. The one or more menu items included in the recommended menu(s) 114 (see FIG. 1) generated in step 208 are based on the one or more recipes.

In one embodiment, food utilization recommendation system 104 (see FIG. 1) uses a classification algorithm to determine a current state of a food item stored in food container 106-1 (see FIG. 1), where the current state has one or more of the following components: storage conditions of the food item, a level of freshness of the food item, a level of staleness of the food item, a predicted shelf life of the food item, and a predicted time of spoilage of the food item. In step 208, food utilization recommendation system 104 (see FIG. 1) generates the recommended menu(s) 114 (see FIG. 1) based on the current state of the food item.

In one embodiment, food utilization recommendation system 104 (see FIG. 1) determines a recommended menu in step 208 that is to be used by an enterprise for a period of time in the future. Food utilization recommendation system 104 (see FIG. 1) determines that one or more food items included in one or more menu items of the recommended menu are not in a current inventory of food items that are available to the enterprise. Based on a consumption profile for the enterprise, the food utilization recommendation system 104 (see FIG. 1) determines an amount of the one or more menu items that are to be prepared in the period of time in the future. The food utilization recommendation system 104 (see FIG. 1) orders the one or more food items so that the one or more food items are included in an updated inventory of food items that are available to the enterprise prior to and during the period of time in the future. The food utilization recommendation system 104 (see FIG. 1) orders the one or more food items in a quantity that is sufficient to prepare the amount of the one or more menu items that are to be prepared in the period of time in the future.

Creating an Estimation Model

Figure 3:
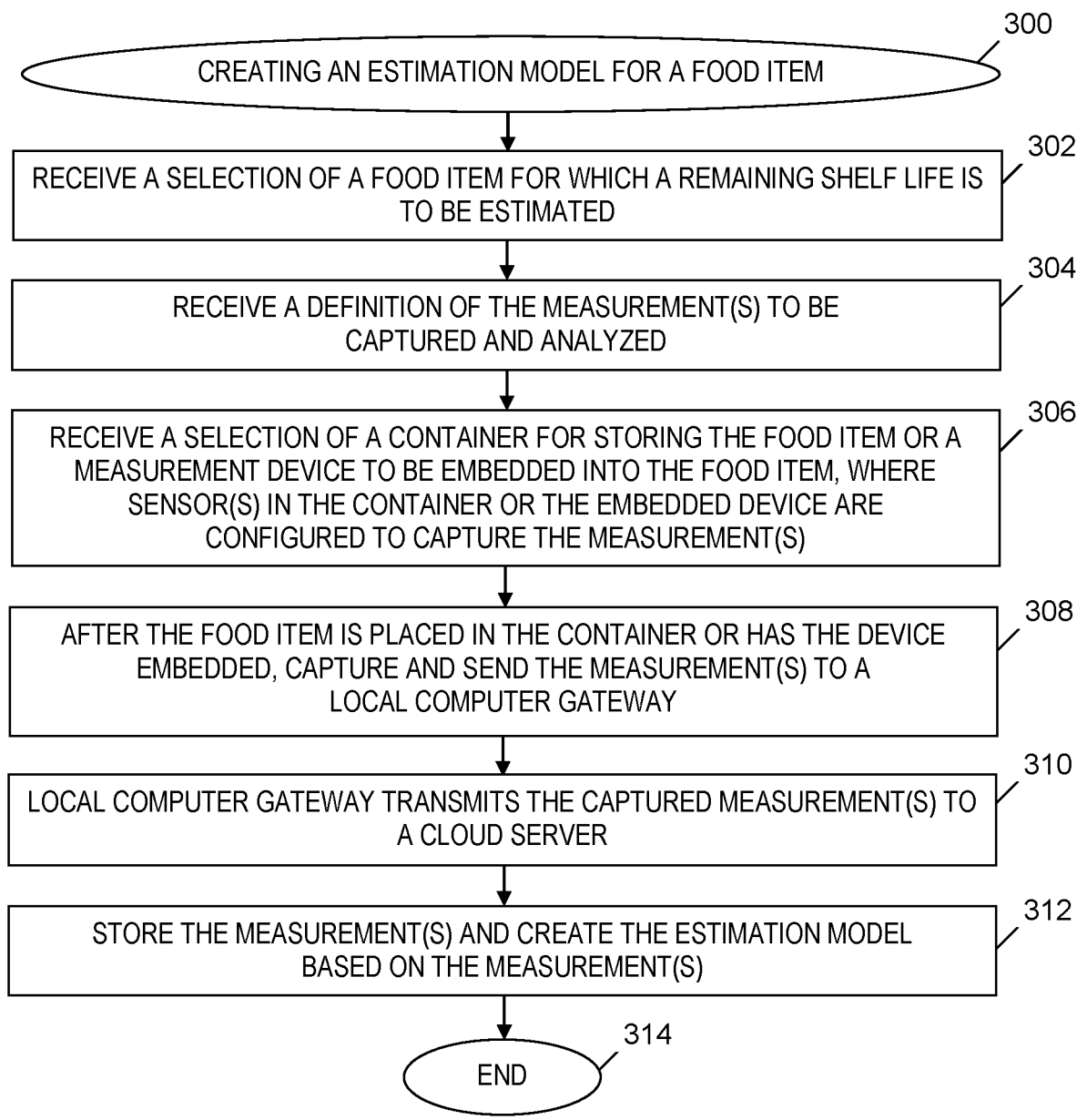
FIG. 3 is a flowchart of a process of creating an estimation model for a food item, where the creation of the estimation model is included in the process of FIG. 2, in accordance with embodiments of the present invention.

FIG. 3 is a flowchart of one embodiment of a process of creating an estimation model for a food item, where the creation of the estimation model is included steps 202 and 204 in the process of FIG. 2, in accordance with embodiments of the present invention. The process of FIG. 3 starts at step 300. In step 302, food utilization recommendation system 104 (see FIG. 1) receives a user-provided selection of a food item for which a remaining shelf life is to be estimated.

In step 304, food utilization recommendation system 104 (see FIG. 1) receives a definition of the measurement(s) to be captured by sensors 108 (see FIG. 1) and analyzed by the machine learning model included in food utilization recommendation system 104 (see FIG. 1).

In step 306, food utilization recommendation system 104 (see FIG. 1) receives a selection of a food container from food containers 106-1, ..., 106-N (see FIG. 1) for storing the selected food item. Sensors 108 (see FIG. 1) in the selected food container are configured to monitor the environmental conditions and/or attributes of the selected food item, which capture the measurement(s) whose definition is received in step 304. Alternatively, a user selects a measurement device to be embedded into the selected food item, where the device includes sensors 108.

In step 308, after the selected food item is placed in the selected food container or has the measurement device embedded, sensors 108 (see FIG. 1) capture the measurement(s) of the environmental conditions and/or attributes of the selected food item and send the measurement(s) to a local computer gateway.

In step 310, the local computer gateway transmits the captured measurement(s) to food utilization recommendation system 104 (see FIG. 1), which is executed in a cloud server.

In step 312, food utilization recommendation system 104 (see FIG. 1) stores the measurement(s) in a data repository and creates an estimation model that includes a prediction function that estimates the remaining shelf life of the selected food item. The estimated remaining shelf life of the selected food item is based on the measurement(s).

After step 312, the process of FIG. 3 ends at step 314.

As an example of the process of FIG. 3, step 302 includes receiving a selection of a banana bunch as the food item for which a remaining shelf life is to be estimated. Human-derived research provides a hypothesis that the banana's appearance (i.e., color and patterns on the surface of the banana) is a factor in determining whether the banana is suitable for consumption, and that storage conditions including air temperature and humidity in the food container and the amount of light to which the banana is exposed are the main factors to be included in the prediction function. Definitions of the measurements that indicate the banana's appearance and storage condition are received in step 304. A machine learning tool such as a visual recognition service included in food utilization recommendation system 104 (see FIG. 1) captures the measurements in a training phase in step 308 to classify the state of the banana bunch based on appearance. For example, ten discrete states of appearance may be defined (e.g., from green to brown/black). Images of bananas in different states of appearance are studied by one or more humans and the images are manually classified into respective states included in the ten discrete states. The human(s) also determine which states of appearance indicate that the banana is suitable for consumption and which other states of appearance indicate that the banana is unsuitable for consumption. This manual classification provides a baseline for the machine learning tool. After the baseline is provided, a new image of a banana is input into the machine learning tool, which classifies the banana into one of the ten states. The particular classification of the banana indicates whether the banana is suitable or unsuitable for consumption.

Furthermore, image classification provides inputs to the estimation model and prediction function of the banana. Measurements of environmental conditions, including air temperature, humidity and amount of light to which the banana is exposed, are additional inputs to the estimation model of the banana, so that an effect of each of the environmental conditions can be proved or disproved. The image classification and environmental conditions measurements are input to a deep learning neural network included in food utilization recommendation system 104 (see FIG. 1). Supervised learning is included in the analysis of the measurements and image classification because a human is needed to rate whether the banana is suitable or unsuitable for consumption.

To facilitate the accuracy of the results of the estimation model of the banana, the data set must be large enough and contain data diversity (e.g., data from bananas stored at different temperatures, different levels of humidity, etc.), so that training data is in a range of expected operational data.

In one embodiment, the output of the estimation model created in step 312 is a model file, such as CORE ML, or a similar format, where the file is instantiated to receive data from a given storage container that stores the banana bunch. For additional banana storage containers, additional respective estimation model instances are necessary so that the estimation model can retain the history of a given storage container.

The estimation model created in step 312 for the selected food item outputs the current consumption state of the selected food item, as well as the amount of time in the remaining shelf life of the selected food item. Again, in one embodiment, the output of the estimation model is an array that associates different food preparation methods applied to the selected food item and whether the selected food item is suitable or unsuitable for consumption. For example, even though a banana may be too ripe for eating it raw, the banana may be used in a smoothie with not noticeable change in flavor.

The process of FIG. 3 is repeated for other food items whose remaining shelf lives are of interest, so that in the remaining steps in the process of FIG. 2, food utilization recommendation system 104 (see FIG. 1) uses multiple estimation models, where one estimation model corresponds to one type of food item.

EXAMPLES

Figure 4:
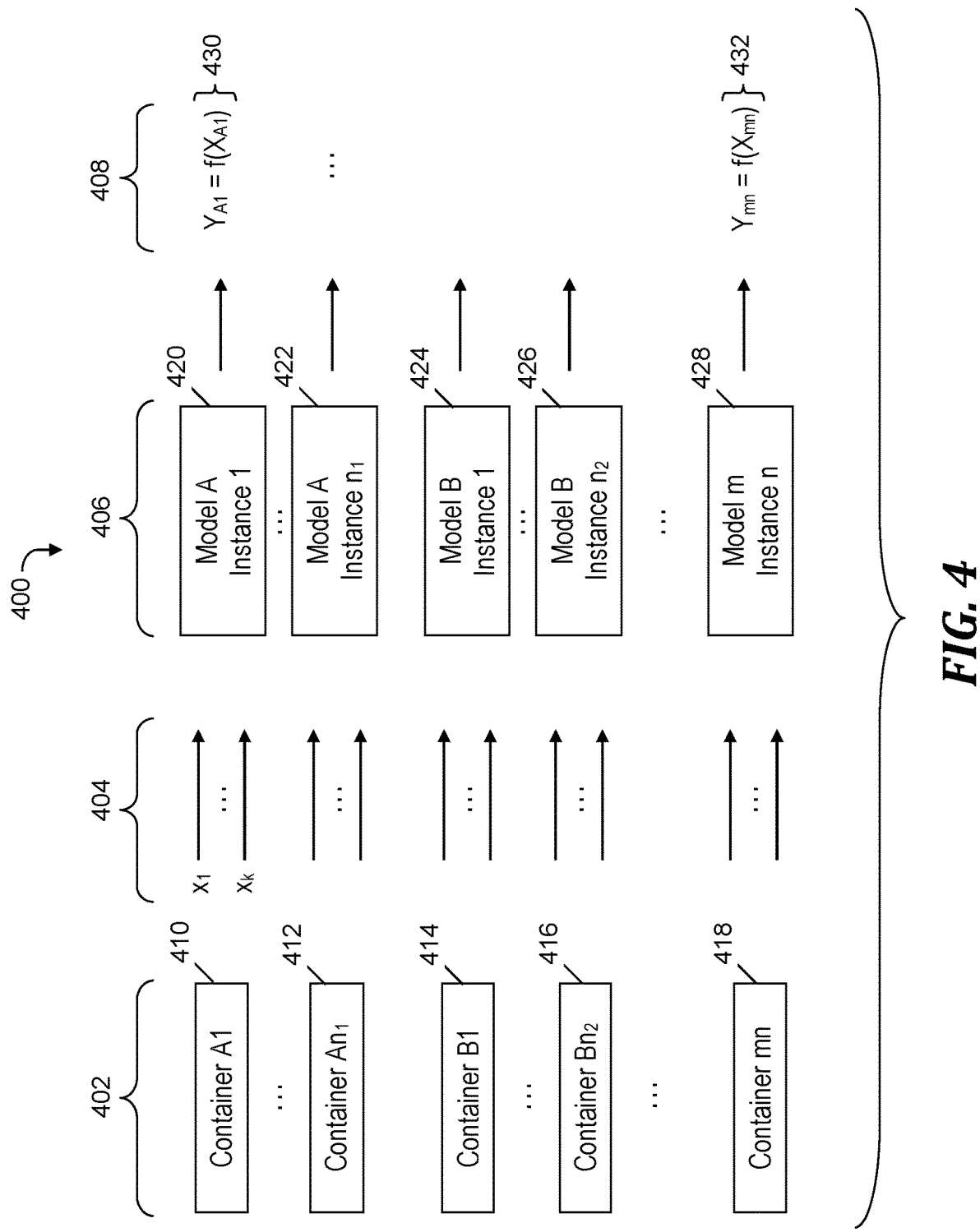
FIG. 4 is an example of generating prediction functions in estimation models used in the process of FIG. 2, in accordance with embodiments of the present invention.

FIG. 4 is an example 400 of generating prediction functions in estimation models used in the process of FIG. 2, in accordance with embodiments of the present invention. A plurality of food containers 402 include sensors that output measurements 404 of environmental conditions and/or attributes of food items stored in food containers 402. Measurements 404 are input to estimation model instances 406, which include prediction functions 408.

Food containers 402 include a first set of food containers 410, . . . , 412 (i.e., food containers A1, . . . , $An_1$, which are of a first type of container), a second set of food containers 414, . . . , 416 (i.e., food containers B1, . . . , $Bn_2$, which are of a second type of container), . . . , food container 418 (i.e., food container mn), etc., where each food container of one type of container is instrumented with sensors for collecting measurements of environmental conditions and/or attributes of a specific type of food item. For example, food containers A1, . . . , $An_1$ are instrumented for bananas and food containers B1, . . . , $Bn_2$ are instrumented for apples. There may be one or more food containers of each type (i.e., $n_1$, $n_2$, etc. are integers greater than or equal to one).

For example, measurements 404 include measurements $x_1, \ldots, x_k$ being collected by sensors in food container A1, where k is an integer and k≥1. The number of measurements for a particular type of food container matches the number of sensors in the food container. The number sensors may vary between different types of food containers, so the number of measurements in measurements 404 provided by sensors in food container A1 (i.e., k measurements) may be the same or different from the number of measurements in measurements 404 provided by sensors in food container B1.

A given food container outputs a set of measurements that becomes input to an estimation model designed for the specific type of food item being stored in the given food container. Instances of a food container provide respective sets of measurements to respective estimation model instances, so that each estimation model instance has historical data (i.e., a memory) about the previous state of the food item associated with the estimation model instance. Having knowledge of the historical data provides a more accurate prediction of remaining shelf life as compared to a stateless model.

For example, food container A1 provides measurements $x_1, \ldots, x_k$ as input to an estimation model instance 420 (i.e., Model A Instance 1) and food container $An_1$ provides measurements as input to an estimation model instance 422, where estimation model instances 420 and 422 are both of type "Model A," which is the type of model designed to analyze bananas.

Similarly, food container B1 provides measurements as input to an estimation model instance 424, food container $Bn_2$ provides measurements as input to an estimation model instance 426, and food container mn provides measurements as input to an estimation model instance 428.

Each estimation model instance has a prediction function that specifies one or more timelines during which the associated food item is suitable for consumption given that the food item is prepared using respective one or more food preparation methods. Solutions of the prediction functions are generated in step 206 (see FIG. 2). For example, estimation model instance 420 includes prediction function 430, where $X_{A1}$ includes the measurements $x_1, \ldots, x_k$. As another example, estimation model instance 428 includes prediction function 432.

Figure 5:
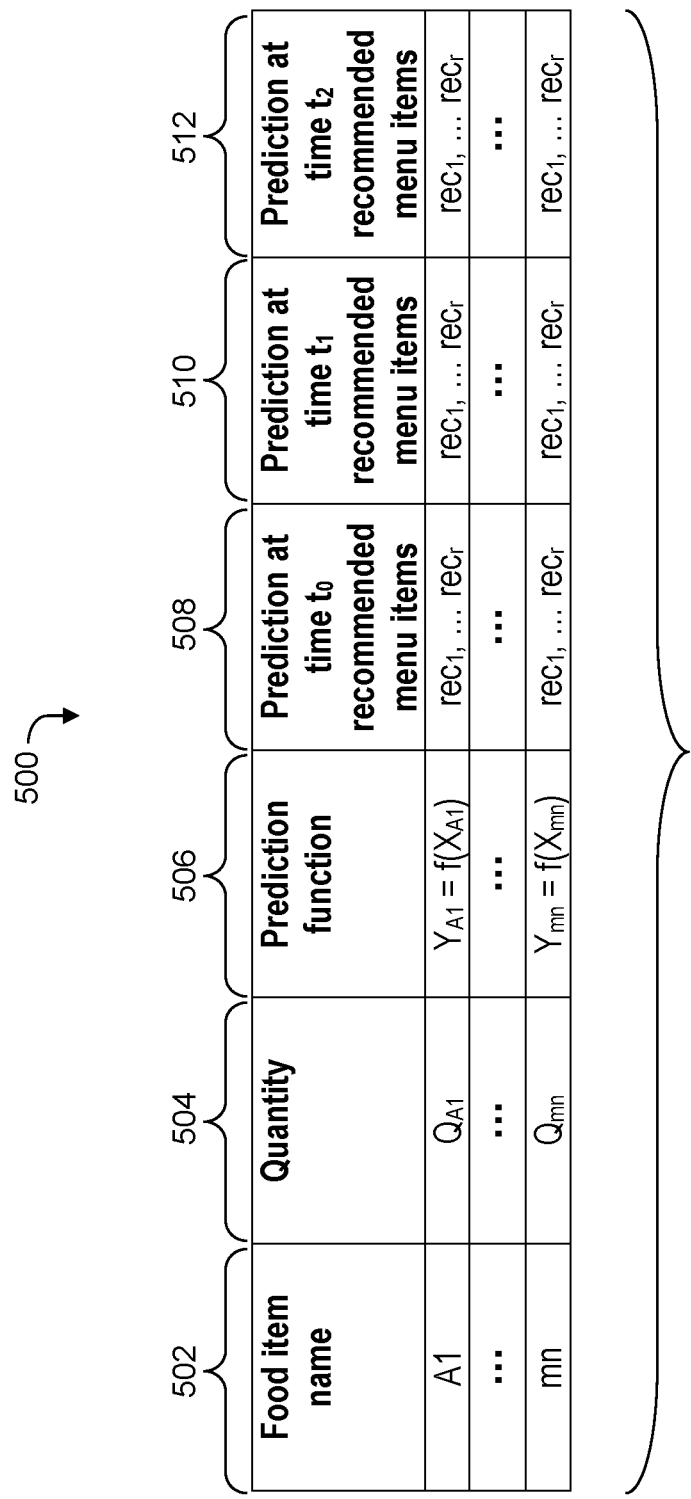
FIG. 5 is an example of a table of an ingredient inventory, prediction functions, and recommended menu items used in the process of FIG. 2, in accordance with embodiments of the present invention.

FIG. 5 is an example of a table 500 of an ingredient inventory, prediction functions, and recommended menu items used in the process of FIG. 2, in accordance with embodiments of the present invention. For multiple food items in a food item inventory, table 500 includes names 502 of the food items, quantities 504 of the food items that are available for consumption, prediction functions 506 that specify timelines during which the food items are suitable for consumption. First solutions 508 of respective prediction functions for a first time (i.e., time $t_0$) indicate respective recommended menu items that include the respective food items. For example, $rec_1, \ldots, rec_r$ in the first data row in the first solutions 508 column are recommendations of menu items that include food item A1. Similarly, second solutions 510 of respective prediction functions for a second time (i.e., time $t_1$) indicate respective recommended menu items that include the respective food items and third solutions 512 of respective prediction functions for a third time (i.e., time $t_2$) indicate respective recommended menu items that include the respective food items. Although table 500 represents the menu item recommendations in solutions 508, 510, and 512 as the identical set of "$rec_1, \ldots, rec_r$," each set of menu item recommendations in table 500 does not necessarily consist of the same recommendations. The menu item recommendations in given sets of menu item recommendations in table 500 may be the same recommendations, all different recommendations, or a combination of recommendation(s) that are the same and other recommendation(s) that are different. Further, the number of menu item recommendations in given sets of menu item recommendations in table 500 may be the same number or different numbers of recommendations. These solutions of the prediction functions are the basis for the recommended menu(s) 114 (see FIG. 1) generated in step 208 (see FIG. 2).

Computer System

Figure 6:
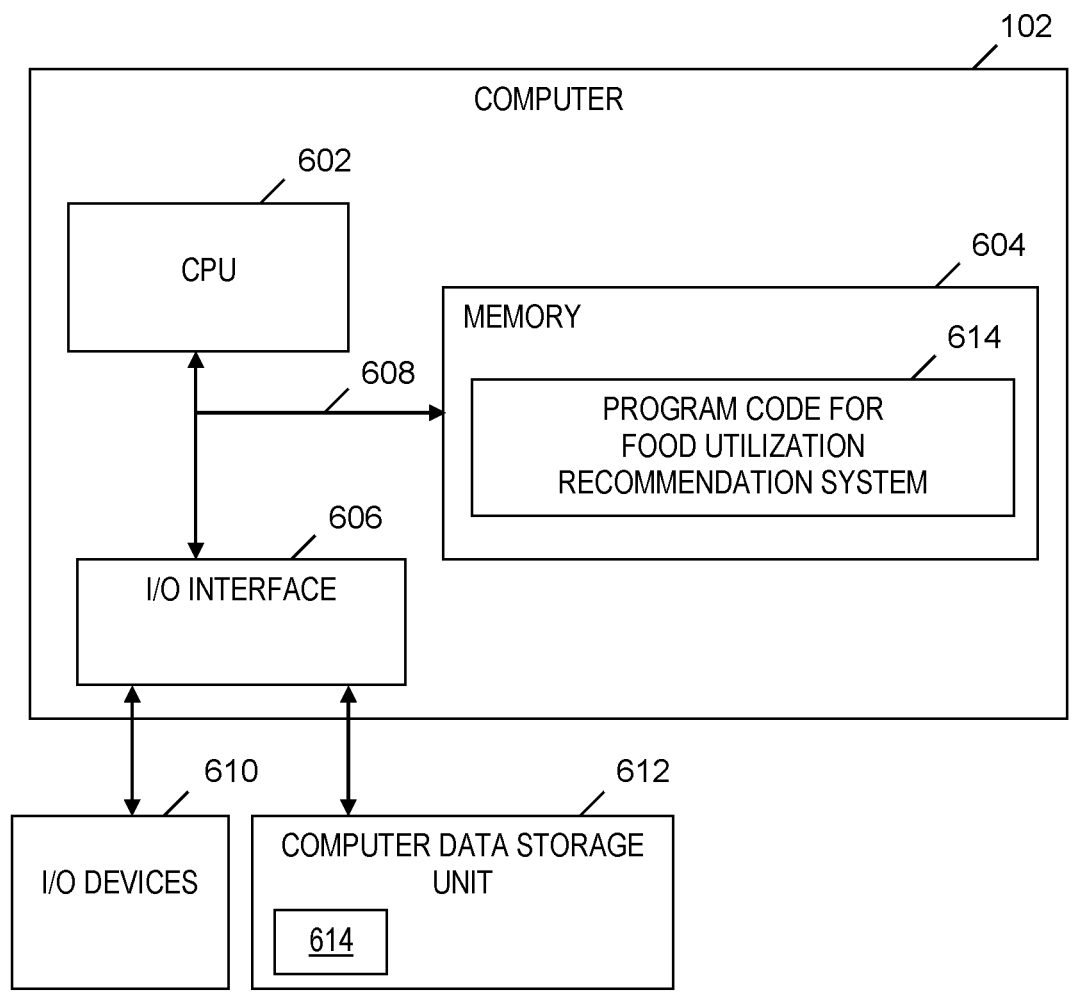
FIG. 6 is a block diagram of a computer included in the system of FIG. 1 and that implements the process of FIG. 2, in accordance with embodiments of the present invention.

FIG. 6 is a block diagram of a computer 102 included in system 100 of FIG. 1 and that implements the process of FIG. 2, in accordance with embodiments of the present invention. Computer 102 is a computer system that generally includes a central processing unit (CPU) 602, a memory 604, an input/output (I/O) interface 606, and a bus 608. Further, computer 102 is coupled to I/O devices 610 and a computer data storage unit 612. CPU 602 performs computation and control functions of computer 102, including executing instructions included in program code 614 for a system that includes food utilization recommendation system 104 (see FIG. 1) to perform a method of reducing food waste by using a machine learning model, where the instructions are executed by CPU 602 via memory 604. CPU 602 may include a single processing unit or be distributed across one or more processing units in one or more locations (e.g., on a client and server).

Memory 604 includes a known computer readable storage medium, which is described below. In one embodiment, cache memory elements of memory 604 provide temporary storage of at least some program code (e.g., program code 614) in order to reduce the number of times code must be retrieved from bulk storage while instructions of the program code are executed. Moreover, similar to CPU 602, memory 604 may reside at a single physical location, including one or more types of data storage, or be distributed across a plurality of physical systems in various forms. Further, memory 604 can include data distributed across, for example, a local area network (LAN) or a wide area network (WAN).

I/O interface 606 includes any system for exchanging information to or from an external source. I/O devices 610 include any known type of external device, including a display, keyboard, etc. Bus 608 provides a communication link between each of the components in computer 102, and may include any type of transmission link, including electrical, optical, wireless, etc.

I/O interface 606 also allows computer 102 to store information (e.g., data or program instructions such as program code 614) on and retrieve the information from computer data storage unit 612 or another computer data storage unit (not shown). Computer data storage unit 612 includes a known computer readable storage medium, which is described below. In one embodiment, computer data storage unit 612 is a non-volatile data storage device, such as a magnetic disk drive (i.e., hard disk drive) or an optical disc drive (e.g., a CD-ROM drive which receives a CD-ROM disk).

Memory 604 and/or storage unit 612 may store computer program code 614 that includes instructions that are executed by CPU 602 via memory 604 to reduce food waste by using a machine learning model. Although FIG. 6 depicts memory 604 as including program code, the present invention contemplates embodiments in which memory 604 does not include all of code 614 simultaneously, but instead at one time includes only a portion of code 614.

Further, memory 604 may include an operating system (not shown) and may include other systems not shown in FIG. 6.

In one embodiment, computer data storage unit 612 includes menu items 110 (see FIG. 1) and ingredient inventory 112 (see FIG. 1).

As will be appreciated by one skilled in the art, in a first embodiment, the present invention may be a method; in a second embodiment, the present invention may be a system; and in a third embodiment, the present invention may be a computer program product.

Any of the components of an embodiment of the present invention can be deployed, managed, serviced, etc. by a service provider that offers to deploy or integrate computing infrastructure with respect to reduce food waste by using a machine learning model. Thus, an embodiment of the present invention discloses a process for supporting computer infrastructure, where the process includes providing at least one support service for at least one of integrating, hosting, maintaining and deploying computer-readable code (e.g., program code 614) in a computer system (e.g., computer 102) including one or more processors (e.g., CPU 602), wherein the processor(s) carry out instructions contained in the code causing the computer system to reduce food waste by using a machine learning model. Another embodiment discloses a process for supporting computer infrastructure, where the process includes integrating computer-readable program code into a computer system including a processor. The step of integrating includes storing the program code in a computer-readable storage device of the computer system through use of the processor. The program code, upon being executed by the processor, implements a method of reducing food waste by using a machine learning model.

While it is understood that program code 614 for reducing food waste by using a machine learning model may be deployed by manually loading directly in client, server and proxy computers (not shown) via loading a computer-readable storage medium (e.g., computer data storage unit 612), program code 614 may also be automatically or semi-automatically deployed into computer 102 by sending program code 614 to a central server or a group of central servers. Program code 614 is then downloaded into client computers (e.g., computer 102) that will execute program code 614. Alternatively, program code 614 is sent directly to the client computer via e-mail. Program code 614 is then either detached to a directory on the client computer or loaded into a directory on the client computer by a button on the e-mail that executes a program that detaches program code 614 into a directory. Another alternative is to send program code 614 directly to a directory on the client computer hard drive. In a case in which there are proxy servers, the process selects the proxy server code, determines on which computers to place the proxy servers' code, transmits the proxy server code, and then installs the proxy server code on the proxy computer. Program code 614 is transmitted to the proxy server and then it is stored on the proxy server.

Another embodiment of the invention provides a method that performs the process steps on a subscription, advertising and/or fee basis. That is, a service provider can offer to create, maintain, support, etc. a process of reducing food waste by using a machine learning model. In this case, the service provider can create, maintain, support, etc. a computer infrastructure that performs the process steps for one or more customers. In return, the service provider can receive payment from the customer(s) under a subscription and/or fee agreement, and/or the service provider can receive payment from the sale of advertising content to one or more third parties.

The present invention may be a system, a method, and/or a computer program product at any possible technical detail level of integration. The computer program product may include a computer readable storage medium (or media) (i.e., memory 604 and computer data storage unit 612) having computer readable program instructions 614 thereon for causing a processor (e.g., CPU 602) to carry out aspects of the present invention.

The computer readable storage medium can be a tangible device that can retain and store instructions (e.g., program code 614) for use by an instruction execution device (e.g., computer 102). The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions (e.g., program code 614) described herein can be downloaded to respective computing/processing devices (e.g., computer 102) from a computer readable storage medium or to an external computer or external storage device (e.g., computer data storage unit 612) via a network (not shown), for example, the Internet, a local area network, a wide area network and/or a wireless network. The network may comprise copper transmission cables, optical transmission fibers, wireless transmission, routers, firewalls, switches, gateway computers and/or edge servers. A network adapter card (not shown) or network interface (not shown) in each computing/processing device receives computer readable program instructions from the network and forwards the computer readable program instructions for storage in a computer readable storage medium within the respective computing/processing device.

Computer readable program instructions (e.g., program code 614) for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations (e.g., FIG. 2) and/or block diagrams (e.g., FIG. 1 and FIG. 6) of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions (e.g., program code 614).

These computer readable program instructions may be provided to a processor (e.g., CPU 602) of a general purpose computer, special purpose computer, or other programmable data processing apparatus (e.g., computer 102) to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium (e.g., computer data storage unit 612) that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions (e.g., program code 614) may also be loaded onto a computer (e.g. computer 102), other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A method of using a machine learning model to reduce food waste, the method comprising:

creating, by one or more processors, estimation models for respective food items by using a machine learning model that receives data from one or more sensors monitoring the food items, the estimation models having respective prediction functions, each prediction function specifying one or more timelines during which a given food item is not spoiled and is in a condition for consumption using respective one or more methods of preparing the given food item;

generating, by the one or more processors, solutions of the prediction functions for a specified inventory of the food items and specified periods of time, the solutions indicating menu items for respective periods of time, each menu item including one or more of the food items which are in the condition for consumption based on the timelines specified by the estimation models;

generating, by the one or more processors and based on the solutions of the prediction functions and the machine learning model, recommendations of menus of a restaurant, the menus corresponding to the specified periods of time, each menu for a given period of time including one or more of the menu items indicated by the solutions of the prediction functions, the recommendations of the menus reducing a waste of the food items through spoilage by increasing a likelihood of a consumption of the food items within the respective timelines, the consumption of the food items being by customers of the restaurant who order the food items after viewing the menus of the restaurant;

determining, by the one or more processors, a remaining inventory of food items that are included in the specified inventory of food items but are not included in current menu items that are included in the menu items indicated by the solutions of the prediction functions; and determining, by the one or more processors and using a cognitive application programming interface (API), one or more new menu items not included in the current menu items by matching the remaining inventory of food items to one or more recipes in a corpus of recipes, the one or more new menu items being determined to minimize a waste of the remaining inventory of food items through spoilage.

2. The method of claim 1, further comprising receiving, by the one or more processors and from a sensor included in the one or more sensors, a measurement indicating an amount of light to which a second food item is exposed, wherein a second estimation model that is for the second food item and is included in the estimation models is based on the received measurement indicating the amount of light to which the second food item is exposed.

3. The method of claim 1, further comprising receiving, by the one or more processors and from a sensor included in the one or more sensors, data indicating a percentage of light reflected from a second food item, wherein a second estimation model that is for the second food item and is included in the estimation models is based on the received data indicating the percentage of light reflected from the second food item.

4. The method of claim 1, further comprising:
determining, by the one or more processors, an adjustment to a combination of a temperature, humidity, and an amount of light in an environment of a food item included in the food items; and
determining, by the one or more processors and using a classification algorithm, that the adjustment to the environment of the food item extends a shelf life of the food item and prevents a spoilage of the food item beyond a time at which the spoilage of the food item is predicted, the time being determined by a prediction function in an estimation model included in the estimation models without taking into account the adjustment to the environment of the food item, wherein the recommendations of the menus is based on the extended shelf life of the food item based on the adjustment to the environment of the food item.

5. The method of claim 1, further comprising:
determining, by the one or more processors, one or more food items having an attribute measurement that is within a threshold amount of a measurement selected from the group consisting of a level of freshness, a level of staleness, a predicted shelf life, and a predicted time of spoilage; and
determining, by the one or more processors, one or more recipes that use the one or more food items having the attribute measurement that is within the threshold amount, wherein one or more menu items included in the menu items are based on the one or more recipes.

6. The method of claim 1, further comprising determining, by the one or more processors and using a classification algorithm, a current state of a food item included in the food items, the current state having one or more components selected from the group consisting of storage conditions of food item, a level of freshness of the food item, a level of staleness of the food item, a predicted shelf life of the food item, and a predicted time of spoilage of the food item, wherein the recommendations of the menus are based on the current state of the food item.

7. The method of claim 1, further comprising:
determining, by the one or more processors, that a menu included in the menus is for a period of time in the future;
determining, by the one or more processors, that one or more food items included in one or more menu items of the menu are not in a current inventory of food items for the restaurant;
determining, by the one or more processors and based on a consumption profile for the restaurant, an amount of the one or more menu items that are to be prepared in the period of time in the future; and
ordering, by the one or more processors, the one or more food items so that the one or more food items are available to the restaurant prior to the period of time in the future, and ordering the one or more food items in a quantity sufficient to prepare the amount of the one or more menu items that are to be prepared in the period of time in the future.

8. The method of claim 1, further comprising the step of:
providing at least one support service for at least one of creating, integrating, hosting, maintaining, and deploying computer readable program code in the computer, the program code being executed by a processor of the computer to implement creating the estimation models, generating the solutions of the prediction functions, generating the recommendations of the menus, determining the remaining inventory of food items, and determining the one or more new menu items.

9. A computer program product for using a machine learning model to reduce food waste, the computer program product comprising a computer readable storage medium having computer readable program code stored on the computer readable storage medium, the computer readable program code being executed by a central processing unit (CPU) of a computer system to cause the computer system to perform a method comprising the steps of:
the computer system creating estimation models for respective food items by using a machine learning model that receives data from one or more sensors monitoring the food items, the estimation models having respective prediction functions, each prediction function specifying one or more timelines during which a given food item is not spoiled and is in a condition for consumption using respective one or more methods of preparing the given food item;
the computer system generating solutions of the prediction functions for a specified inventory of the food items and specified periods of time, the solutions indicating menu items for respective periods of time, each menu item including one or more of the food items which are in the condition for consumption based on the timelines specified by the estimation models;
based on the solutions of the prediction functions and the machine learning model, the computer system generating recommendations of menus of a restaurant, the menus corresponding to the specified periods of time, each menu for a given period of time including one or more of the menu items indicated by the solutions of the prediction functions, the recommendations of the menus reducing a waste of the food items through spoilage by increasing a likelihood of a consumption of the food items within the respective timelines, the consumption of the food items being by customers of the restaurant who order the food items after viewing the menus of the restaurant;
the computer system determining a remaining inventory of food items that are included in the specified inventory of food items but are not included in current menu items that are included in the menu items indicated by the solutions of the prediction functions; and using a cognitive application programming interface (API), the computer system determining one or more new menu items not included in the current menu items by matching the remaining inventory of food items to one or more recipes in a corpus of recipes, the one or more new menu items being determined to minimize a waste of the remaining inventory of food items through spoilage.

10. The computer program product of claim 9, wherein the method further comprises the computer system receiving, from a sensor included in the one or more sensors, a measurement indicating an amount of light to which a second food item is exposed, wherein a second estimation model that is for the second food item and is included in the estimation models is based on the received measurement indicating the amount of light to which the second food item is exposed.

11. The computer program product of claim 9, wherein the method further comprises the computer system receiving, from a sensor included in the one or more sensors, data indicating a percentage of light reflected from a second food item, wherein a second estimation model that is for the second food item and is included in the estimation models is based on the received data indicating the percentage of light reflected from the second food item.

12. The computer program product of claim 9, wherein the method further comprises:
the computer system determining an adjustment to a combination of a temperature, humidity, and an amount of light in an environment of a food item included in the food items; and
using a classification algorithm, the computer system determining that the adjustment to the environment of the food item extends a shelf life of the food item and prevents a spoilage of the food item beyond a time at which the spoilage of the food item is predicted, the time being determined by a prediction function in an estimation model included in the estimation models without taking into account the adjustment to the environment of the food item, wherein the recommendations of the menus is based on the extended shelf life of the food item based on the adjustment to the environment of the food item.

13. The computer program product of claim 9, wherein the method further comprises:
the computer system determining one or more food items having an attribute measurement that is within a threshold amount of a measurement selected from the group consisting of a level of freshness, a level of staleness, a predicted shelf life, and a predicted time of spoilage; and
the computer system determining one or more recipes that use the one or more food items having the attribute measurement that is within the threshold amount, wherein one or more menu items included in the menu items are based on the one or more recipes.

14. A computer system comprising:
a central processing unit (CPU);
a memory coupled to the CPU; and
a computer readable storage device coupled to the CPU, the computer readable storage device containing instructions that are executed by the CPU via the memory to implement a method of using a machine learning model to reduce food waste, the method comprising the steps of:
the computer system creating estimation models for respective food items by using a machine learning model that receives data from one or more sensors monitoring the food items, the estimation models having respective prediction functions, each prediction function specifying one or more timelines during which a given food item is not spoiled and is in a condition for consumption using respective one or more methods of preparing the given food item;
the computer system generating solutions of the prediction functions for a specified inventory of the food items and specified periods of time, the solutions indicating menu items for respective periods of time, each menu item including one or more of the food items which are in the condition for consumption based on the timelines specified by the estimation models;
based on the solutions of the prediction functions and the machine learning model, the computer system generating recommendations of menus of a restaurant, the menus corresponding to the specified periods of time, each menu for a given period of time including one or more of the menu items indicated by the solutions of the prediction functions, the recommendations of the menus reducing a waste of the food items through spoilage by increasing a likelihood of a consumption of the food items within the respective timelines, the consumption of the food items being by customers of the restaurant who order the food items after viewing the menus of the restaurant;
the computer system determining a remaining inventory of food items that are included in the specified inventory of food items but are not included in current menu items that are included in the menu items indicated by the solutions of the prediction functions; and
using a cognitive application programming interface (API), the computer system determining one or more new menu items not included in the current menu items by matching the remaining inventory of food items to one or more recipes in a corpus of recipes, the one or more new menu items being determined to minimize a waste of the remaining inventory of food items through spoilage.

15. The computer system of claim 14, wherein the method further comprises the computer system receiving, from a sensor included in the one or more sensors, a measurement indicating an amount of light to which a second food item is exposed, wherein a second estimation model that is for the second food item and is included in the estimation models is based on the received measurement indicating the amount of light to which the second food item is exposed.

16. The computer system of claim 14, wherein the method further comprises the computer system receiving, from a sensor included in the one or more sensors, data indicating a percentage of light reflected from a second food item, wherein a second estimation model that is for the second food item and is included in the estimation models is based on the received data indicating the percentage of light reflected from the second food item.

17. The computer system of claim 14, wherein the method further comprises:
the computer system determining an adjustment to a combination of a temperature, humidity, and an amount of light in an environment of a food item included in the food items; and
using a classification algorithm, the computer system determining that the adjustment to the environment of the food item extends a shelf life of the food item and prevents a spoilage of the food item beyond a time at which the spoilage of the food item is predicted, the time being determined by a prediction function in an estimation model included in the estimation models without taking into account the adjustment to the environment of the food item, wherein the recommendations of the menus is based on the extended shelf life of the food item based on the adjustment to the environment of the food item.

* * * * *